United States Patent
Do

(10) Patent No.: US 10,865,155 B2
(45) Date of Patent: Dec. 15, 2020

(54) INTERNET OF THINGS (IOT) BIOTOWER (BLOTOWER#) SYSTEM AND PROCESS FOR RECYCLING FOOD WASTES INTO NUTRIENTS FOR GROWING ORGANIC PLANTS

(71) Applicant: Thinh Hoang Do, Ho Chi Minh (VN)

(72) Inventor: Thinh Hoang Do, Ho Chi Minh (VN)

(73) Assignee: Ton Duc Thang University, Ho Chi Minh (VN)

( * ) Notice: Subject to any disclaimer, the term of this patent is extended or adjusted under 35 U.S.C. 154(b) by 0 days.

(21) Appl. No.: 15/482,797

(22) Filed: Apr. 9, 2017

(65) Prior Publication Data

US 2018/0290944 A1 Oct. 11, 2018

(51) Int. Cl.
| | | |
|---|---|---|
| *C05F 17/05* | (2020.01) | |
| *C05F 9/04* | (2006.01) | |
| *C05F 9/02* | (2006.01) | |
| *C05F 17/90* | (2020.01) | |
| *C05F 3/00* | (2006.01) | |
| *C05F 3/06* | (2006.01) | |
| *B09B 3/00* | (2006.01) | |
| *A01K 67/033* | (2006.01) | |
| *A01G 9/02* | (2018.01) | |
| *B09B 5/00* | (2006.01) | |
| *C05F 17/95* | (2020.01) | |
| *C05F 17/993* | (2020.01) | |
| *A01G 27/00* | (2006.01) | |

(52) U.S. Cl.
CPC .......... *C05F 17/05* (2020.01); *A01G 9/023* (2013.01); *A01K 67/0332* (2013.01); *B09B 3/00* (2013.01); *B09B 5/00* (2013.01); *C05F 3/00* (2013.01); *C05F 3/06* (2013.01); *C05F 17/90* (2020.01); *C05F 17/95* (2020.01); *C05F 17/993* (2020.01); *A01G 27/003* (2013.01); *C05F 9/02* (2013.01); *C05F 9/04* (2013.01); *Y02A 40/20* (2018.01); *Y02P 20/145* (2015.11); *Y02W 30/40* (2015.05)

(58) Field of Classification Search
None
See application file for complete search history.

(56) References Cited

U.S. PATENT DOCUMENTS

| | | | | |
|---|---|---|---|---|
| 5,759,224 | A * | 6/1998 | Olivier | A01K 67/033 71/9 |
| 6,001,146 | A * | 12/1999 | Olivier | C05F 17/05 71/9 |
| 6,391,620 | B1 * | 5/2002 | Olivier | C05F 17/05 435/262.5 |
| 2002/0115199 | A1 * | 8/2002 | Thompson | A01K 67/0332 435/290.1 |
| 2010/0236308 | A1 * | 9/2010 | Gunn | C05F 9/00 71/11 |
| 2012/0244611 | A1 * | 9/2012 | Branham | C05F 17/05 435/290.1 |
| 2013/0118410 | A1 * | 5/2013 | Berkson | C05F 17/05 119/6.7 |

* cited by examiner

*Primary Examiner* — Wayne A Langel

(57) ABSTRACT

An Internet of Things (IoT) BIoTower™ for recycling food wastes into nutrients and for growing organic plants is disclosed which includes a food waste disposable tower for receiving food wastes; a multi-leveled carousels connected to the food waste disposable tower, each containing soils infested with earthworms; and an Internet of Things (IoT) irrigation system designed to provide sustainability to the soils and the organic plants.

20 Claims, 9 Drawing Sheets

INTERNET OF THINGS (IOT) BIOTOWER (BLOTOWER#) SYSTEM AND PROCESS FOR RECYCLING FOOD WASTES INTO NUTRIENTS FOR GROWING ORGANIC PLANTS

FIELD OF THE INVENTION

This invention generally relates to a bio-tower. More specifically, this invention relates to a bio-tower controlled by Internet of Things (IoT).

BACKGROUND OF ART

Municipal wastes can be categorically divided into inorganic wastes and organic wastes. When successfully separated from inorganic wastes, organic wastes or green wastes have a fast biodegradable time with a simple recycling process. On the other hand, inorganic wastes take about ten or more years up to hundreds of years to completely disintegrate. However, when the two type of wastes are mixed together, the organic wastes will take longer to decompose, generate very bad odor, and seriously pollute the environment. Furthermore, the admixtures of organic and inorganic wastes further complicate the recycling process and produce impurities in the renewed products. Impurities often degrade the qualities of the renewed products to the point that the renewed products become second generation wastes—wastes that become wastes after a long, complicated, and expensive recycling process.

Many technologies are available to treat organic wastes but they are struggling to find the balance between cost, energy consumption, and effectiveness. Biogas technology require large investments and the products have low energy value for soils. Composting is inexpensive but often results in low value and low yield products for soil treatment. Sanitary land filings is not a viable solution nowadays due to the shortage of lands. Usually, the above mentioned technologies require an extra step of segregating organic wastes and inorganic wastes at the recycling plants. This is because people do not have the natural tendency to separate organic wastes from inorganic wastes. Farmers separate organic wastes to feed their livestock or to make composts for their plants and vegetables. A few city dwellers make composts out of organic wastes for their gardens. But with the shortage of lands and cramping living spaces in the cities, fewer and fewer people have the inclination to separate organic and inorganic wastes.

Therefore, it is essential to classify and segregate organic wastes from inorganic wastes before they are discarded together at the dump sites.

Setting up a worm bin to make compost is time consuming. First, it requires a bin, soil, worms, food for the worms, a cover, and regular watering schedule. People have to water and feed the worms regularly otherwise the worms would die. Furthermore, only people who have a garden would be willing to spend time to set up a worm bin. With the availability of artificial manure in stores, people tend to buy them instead of setting up a worm bins.

Therefore, what is needed is a system and process that encourage people to separate organic wastes from inorganic wastes.

In addition, what is needed is a productive system and process that can effectively recycle organic wastes into nutrients that can grow organic plants and vegetables.

What is needed is a system and process that encourage people to segregate organic food wastes from inorganic wastes and to transform the organic food wastes into bio-nutrients to grow organic foods without requiring considerable time and effort.

SUMMARY OF THE INVENTION

The present invention is directed to providing a system and process for encouraging people to segregate food wastes from inorganic wastes and for recycling the food wastes into nutrients that are healthy and good for organic foods.

According to one aspect of the invention, there is provided a system and process for separating food wastes and recycling the food wastes to grow organic foods without requiring considerable time and effort.

According to another aspect of the invention, there is provided a system and process for separating food wastes, recycling the food wastes to grow organic foods, and at the same time creating a decorative object without using a large amount of lands or a recycling plant.

According to another aspect of the invention, there is provided a system and process that uses today technology and cloud based network such as Internet of things (IoT) to control everywhere and every when the recycling of food wastes into bio nutrients to grow organic plants.

According to another aspect of the invention, there is provided a system and process that uses today technology and cloud based network such as Internet of things (IoT) to control everywhere and every when the recycling of food wastes into bio nutrients to grow organic plants.

According to another aspect of the invention, there is provided a system and process for separating food wastes and recycling the food wastes to grow organic foods that are inexpensive and easy to assemble.

The above objectives of the present invention are achieved by the disclosure of an Internet of Things bio-tower (BIoTower™) that includes a food waste disposable tower for receiving food wastes; a multi-leveled carousels connected to the food waste disposable tower, each containing soils infested with earthworms; and an Internet of Things (IoT) controlled irrigation system designed to provide proper humidity to the soils.

The above objectives of the present invention are achieved by the disclosure of an Internet of Things bio-tower (BIoTower™) that includes a food waste disposable tower for receiving food wastes; a multi-leveled carousels connected to the food waste disposable tower, each containing soils infested with earthworms; and an Internet of Things (IoT) controlled irrigation system designed to provide proper humidity to the soils.

The above objectives of the present invention are achieved by the disclosure of a process comprising the steps of: providing soil areas; providing earthworms to the soil areas; growing organic plants on the soil areas; providing a food waste areas directly contiguous to the soil areas, the food waste areas having a plurality of exit and entry openings so that the earthworms can enter said food waste areas to digest the food wastes and return to the soil areas to deposit nutrients into the soil areas; connecting the food waste areas with an Internet of Things (IoT) processor; and controlling the humidity of the soil areas using a remote device capable of communicating with the IoT processor.

These and other advantages of the present invention will no doubt become obvious to those of ordinary skill in the art after having read the following detailed description of the preferred embodiments, which are illustrated in the various drawing Figures.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE INVENTION

The invention is detail described with reference to the drawings provided as illustrative examples of the invention.

Figure 1:
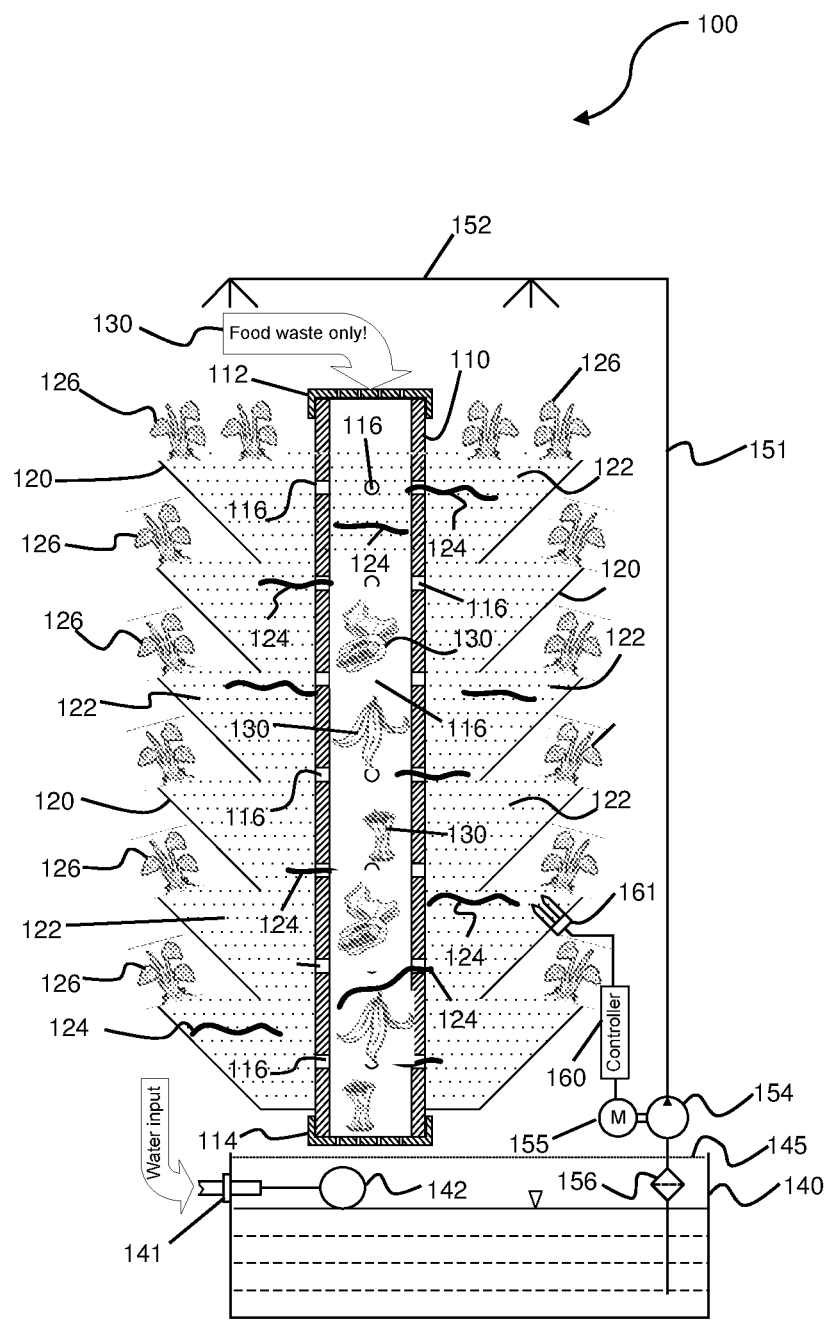
FIG. 1 is a schematic diagram of an Internet of Things (IoT) BIoTower™ in accordance with an exemplary embodiment of the present invention.

Referring now to FIG. 1 which presents an overview of an Internet of Things (IoT) bio-tower (BIoTower™) that encourages the separation and recycling of organic wastes such as food wastes, encourages the growth organic plants, and at the same time create a decorative green object healthy for the environment in accordance with an exemplary embodiment of the present invention is illustrated.

More particularly, FIG. 1 illustrates a schematic diagram of an Internet of Things (IoT) bio-tower (BIoTower™) 100 in accordance with an exemplary embodiment of the present invention. At the heart of BIoTower™ 100 is a food waste disposable tower 110, a multi-leveled carousels 120, and an Internet of Things (IoT) irrigation system including a water container 140, a water tube 151, ring sprinkler 152, a water pump 154, a motor 155, a water filter 156, a humidity and temperature sensor 161, a motor 155 that operates water pump 154, a processor 160 that controls water pump 154. In one illustrating embodiment, processor 160 uses IoT technology over WIFI that receives humidity and temperature data from sensor 161 and transfers the data to a cloud based service. Users can observe the data, set up irrigating humidity and control the pump via smartphones. Processor 160 uses the humidity data to turn on or off water pump 154 via motor 155 to provide proper humidity for earthworms 124 and organic plants 126. Yet, in another illustrating but not limiting embodiment, a cellular phone (not shown) or a computer system can share the humidity and temperature with processor 160 to turn on or off water pump 154.

Continuing with FIG. 1, food waste disposable tower 110 further includes a top cap 112, a bottom cap 114, cylindrical cores 310 and a plurality of entry and exit openings 116 for earthworms 124 to enter and exit therefrom. Food wastes 130 are discarded into food waste disposable tower 120 from the top as shown in FIG. 1. In one illustrating embodiment, food waste disposable tower 110 has a cylindrical shape that includes plurality of entry and exit openings 116 around its lateral perimeter. It is understood by a person of skill in the art that food waste disposable tower 110 can have other geometrical shapes such as semi-circle, square cross section, etc.

Multi-leveled carousels 120 is inserted into food waste disposable tower 110 and extends radially outward. In one illustrating embodiment, multi-carousels 120 comprises a plurality of carousels stacked vertically on top of one another. Soils 122 are deposited into each carousel 120. Multi-carousels 120 surrounds food waste disposable tower 110 and therefore soils 122 also contact and surround plurality entry and exit openings 124. Soils 122 in each carousel 120 are where organic plants 126 are grown, decorated, and home to earthworms 124.

Figure 2:
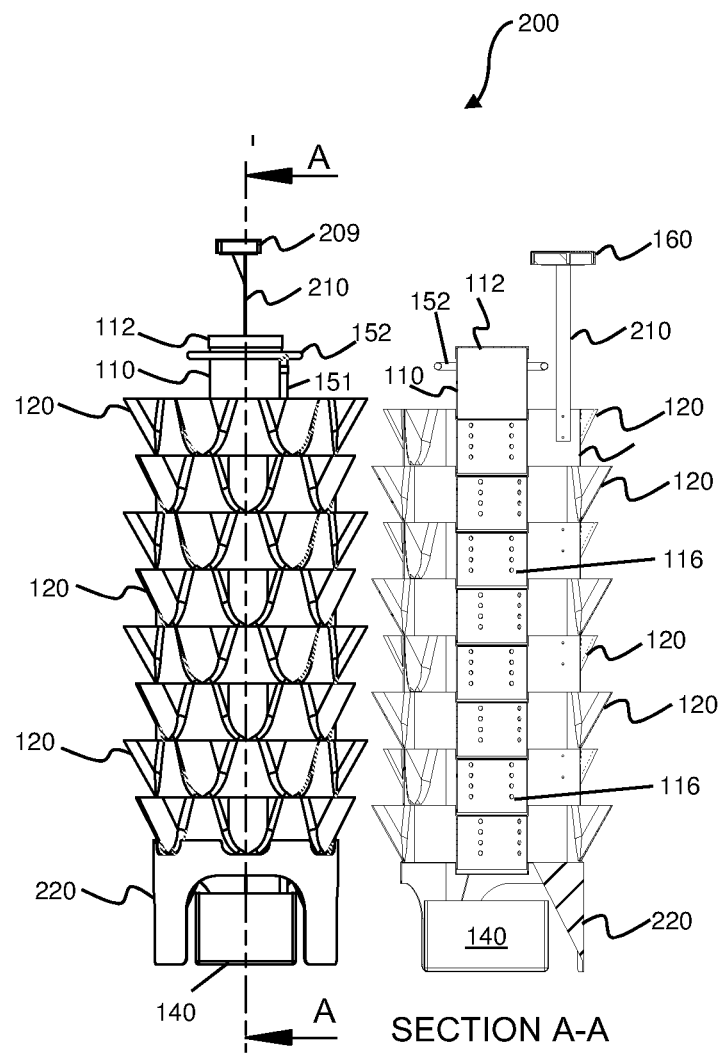
FIG. 2 is a 2-dimension (2D) front view and a cross-sectional view AA of the BIoTower™ in accordance with an exemplary embodiment of the present invention.

Next referring to FIG. 2, a side view and cross-sectional view 200 which show the detailed structure of food waste disposable tower 110 and multi-leveled carousels 120 are illustrated. FIG. 2 further shows that a controller box 209 is positioned on top of a supporting pole 210. In one exemplary embodiment, controller box 209 which contains processor 160 communicates with sensor 161, and motor 155 via electrical cords (not shown) hidden inside supporting pole 210. In another exemplary embodiment, processor 160 communicates with sensor 161 and motor 155 via WIFI and sensor 161 is an Internet of Things (IoT) sensor. It is also shown in FIG. 2 that ring sprinkler 152 encircles food waste disposable tower 110. Water tube 151 connects and pumps water from water container 140 to water soils 122. Multi-leveled carousels 120 encircles both water tube 151 and food waste disposable tower 110 so that soils 122 surround and make direct contact with food waste disposable tower 110. FIG. 2 further illustrates that BIoTower™ 100 further includes a foot stand 220 placed underneath to support multi-leveled carousels 120.

Figure 3A:
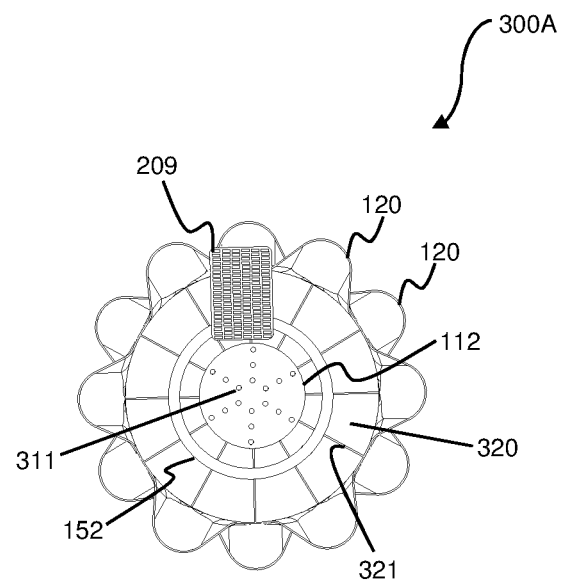
FIG. 3A is a top view of the BIoTower™ of FIG. 1 in accordance with an exemplary embodiment of the present invention.

Next, referring to FIG. 3A illustrating a top view 300A of BIoTower™ 100. As seen from top view 300A, top cap 112 further includes a plurality of holes 311 designed to allow air into food waste disposable tower 110. In one illustrating embodiment, each carousel 120 is divided into wedged sections 320 by dividers 321 arranged diagonally along the radius of food waste disposable tower 110 so that different organic plants 126 can be grown in different wedged section 320.

Figure 3B:
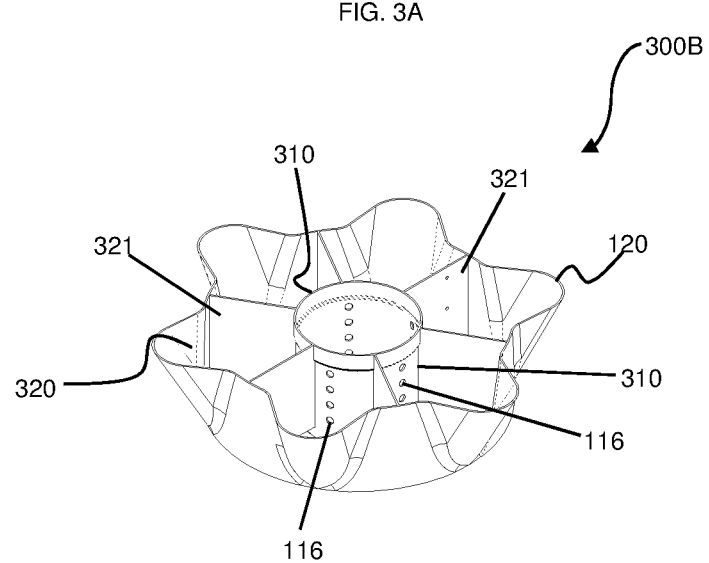
FIG. 3B is a 3-dimension (3D) view of one of the carousels of the BIoTower™ of FIG. 1 in accordance with an exemplary embodiment of the present invention.

FIG. 3B illustrates a three-dimensional (3D) view 300B of each carousel of multi-leveled carousels 120. Each carousel 120 has a cylindrical core where dividers 321 are radiating therefrom to create wedged sections 320. Cylindrical core 310 is inserted into and directly connected to food waste disposable tower 110. Each carousel 120 is inserted one-by-one into food waste disposable tower 110 so that they stack on top of one another form multi-leveled carousels 120. In one illustrating embodiment, each carousel 120 includes a plurality of petal shaped extensions so that each carousel 120 has a shape of a tortilla bowl. Soils 122 are deposited into each wedged section 320 where organic plants 126 grow and earthworms 124 live. Earthworms 124 enter food waste disposable tower 110 through plurality of entry and exit openings 116 to digest food wastes 130. Afterward, they return to carousel 120 to provide a valuable nutrition for soils 122, making soils 122 a better place for organic plants 126.

Figure 4A:
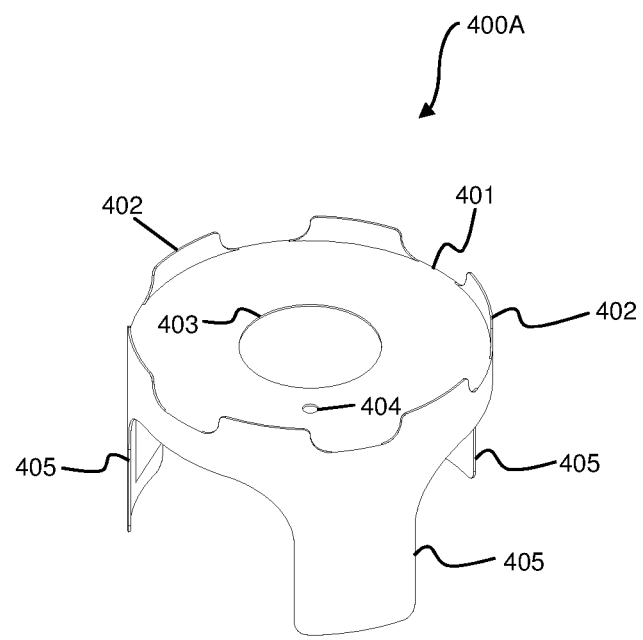
FIG. 4A is a 3-dimension view of the 3 legged stool that support the multi-leveled carousels of the bio-tower in accordance with an exemplary embodiment of the present invention.

Referring now to FIG. 4A, a three-dimension (3D) view 400A of foot stand 220. In one exemplary embodiment, foot stand 220 is a three-legged stool. Foot stand 220 has a top surface 401 and three supporting legs 405. Top surface 401 has a through-hole 403 at the center through which food waste disposable tower 110 is inserted. Next to through-hole 403 is a water-pipe hole through which water pipe 152 is inserted therethrough. Around the outer perimeter of top surface 401, rails 402 are projected upward to prevent multi-leveled carousels 120 from being toppled over.

Figure 4B:
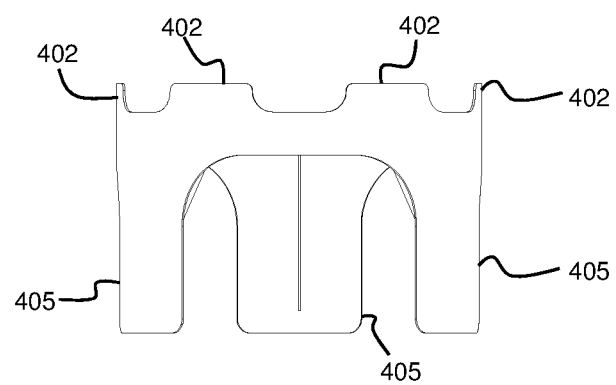
FIG. 4B is a planar view of the 3 legged stool that support the multi-leveled carousels of the BIoTower™ in accordance with an exemplary embodiment of the present invention.

FIG. 4B shows a side view 400B of foot stand 220 which illustrates that foot stand 220 is practically hollow below top surface 401. The hollow space surrounded by three supporting legs 405 is where water container 140 is placed.

Figure 5:
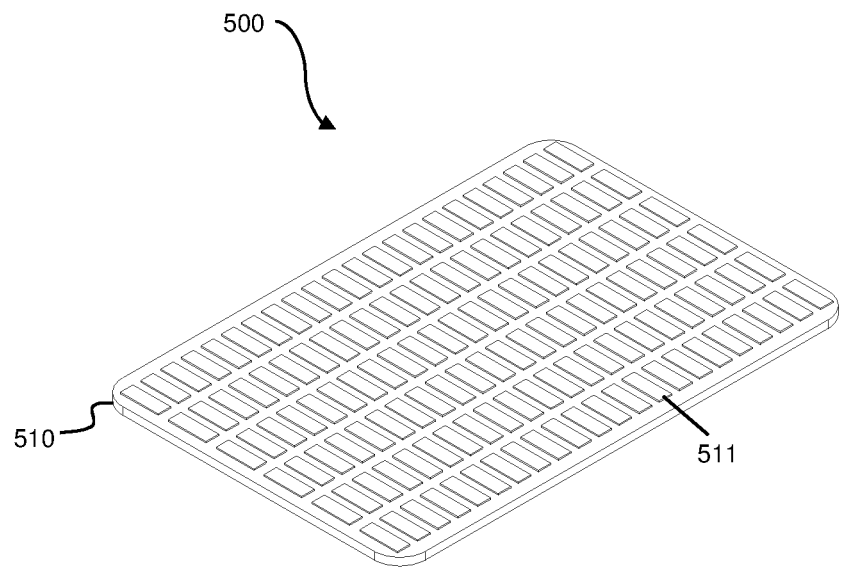
FIG. 5 is a 3 dimension (3D) view of the internal components of the controller box that contains a IoT processor of the BIoTower™ in accordance with an exemplary embodiment of the present invention.
Figure 5:
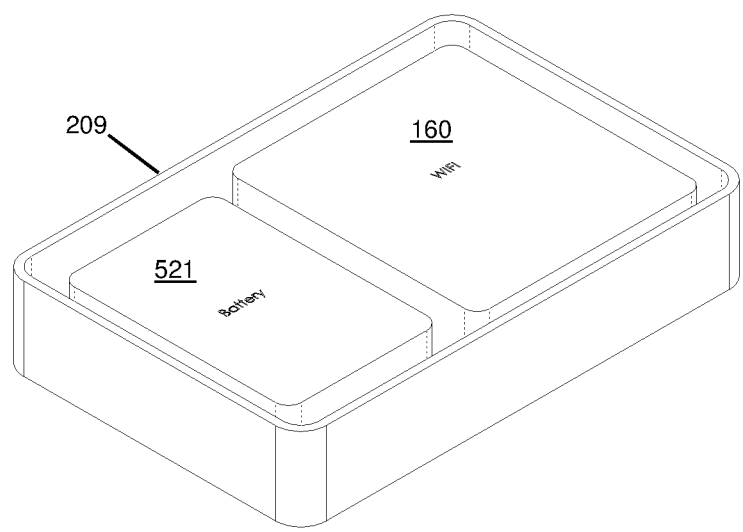

Next referring to FIG. 5, a three-dimension (3D) view 500 of processor 160 illustrated. In an exemplary embodiment, controller box 209 has a solar panel 510 with a plurality of solar cells 511. Solar panel 510 is placed on top as a lid for a controller box 209. Controller box 209 includes a battery 521 and processor 106. In a non-limiting embodiment of the present invention, processor 160 is an Internet of Things (IoT) device which uses WIFI as a communication means. Processor 160 can also uses a Z-wave, Zig-bee, Bluetooth, or radio frequency (RF), optical, etc. as communication protocol. Solar panel 510 collects the sun energy and converts it into electrical energy which is stored in battery 521. Battery 521 is in turn providing voltage supplies to processor 160, sensor 161, motor 15566, water pump 154, and filter 140. All the electrical connections from battery 521 to the above listed electrical components are hidden inside supporting pole 210. Referring back to FIG. 2 and FIG. 3A both show that controller box 209 is erected above food waste disposable tower 160 and faced upward to collect energy from the sun.

Figure 6:
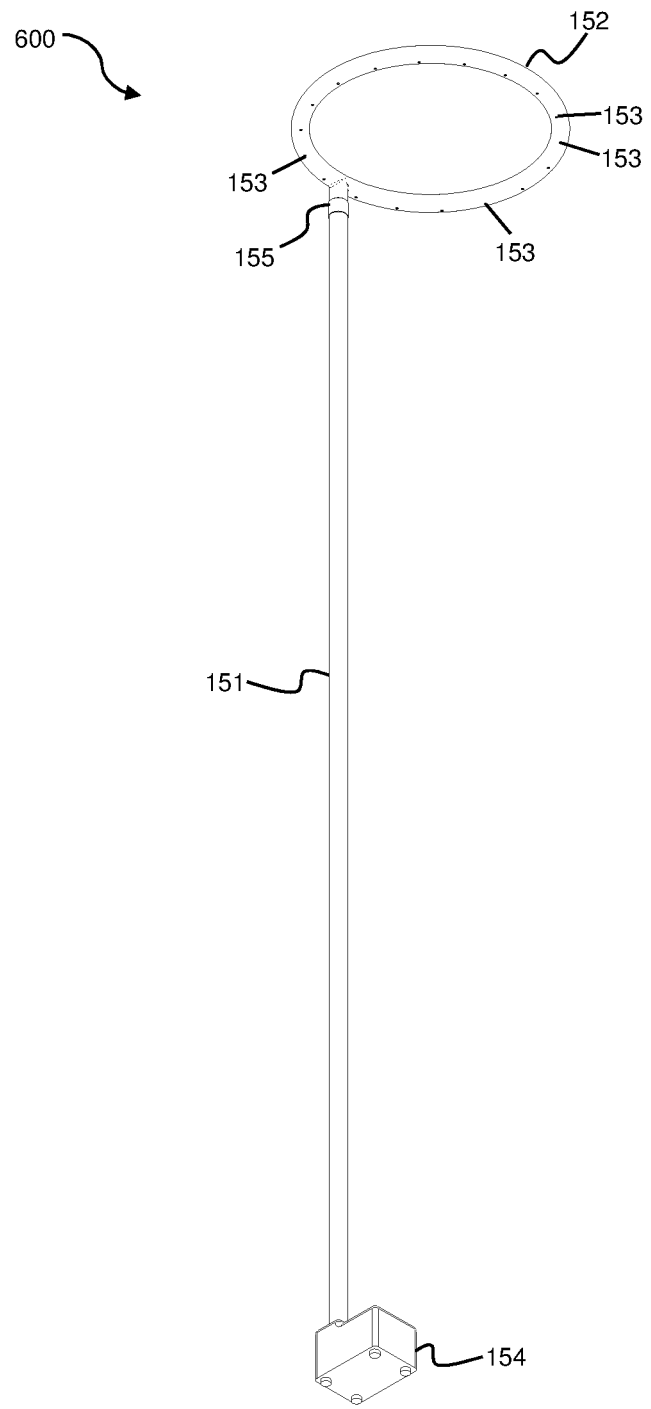
FIG. 6 illustrates a lateral view of the IoT irrigation system of the BIoTower™ of FIG. 1 in accordance with an exemplary embodiment of the present invention.

Referring now to FIG. 6, a three-dimension (3D) view 600 of the top portion of irrigation system discussed in FIG. 1 is illustrated. In this exemplary embodiment, ring sprinkler 152 includes plurality of holes 153 dotted around the circumference of ring sprinkler 152. A connector 155 snuggly connects one end of water pipe 151 to ring sprinkler 152. The other end of water pipe 151 is connected to water pump 154. Water pump 154 is submerged into water container 140 as shown in FIG. 1.

Figure 7:
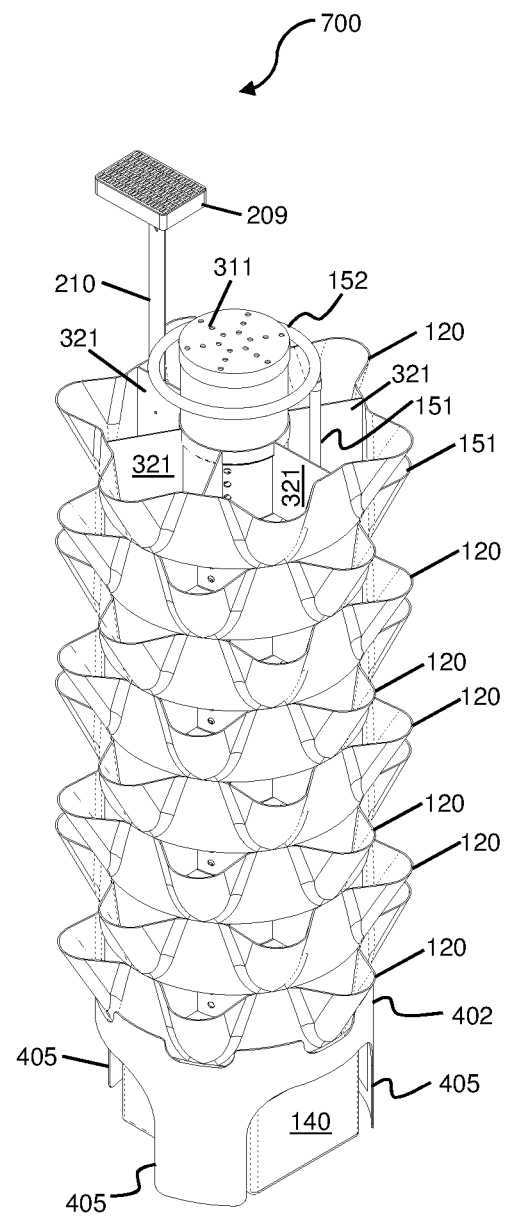
FIG. 7 is a 3D view of the BIoTower™ of FIG. 1 in accordance with an exemplary embodiment of the present invention.

Referring next to FIG. 7, a three-dimension (3D) view 700 of bio-tower 100 is illustrated. In FIG. 7, the operation of bio-tower 100 as illustrated in FIG. 1 is described in details.

Referring back to FIG. 1-FIG. 6, in operation, food wastes 130 are first thrown into food waste disposable tower 110 from the top. Inside food waste disposable tower 110, biodegradable food wastes are broken down by earthworms 124 over time. Earthworms 124 crawl through plurality of entry and exit openings 116 to feed on food wastes 130. As earthworms 124 feed on food wastes 130, organic matter passes through their bodies. When earthworms 124 return to soils 122 through plurality of entry and exit openings 116 they excreted out granular dark castings in soils 122. Earthworm castings are bio-fertilizer which is rich in nutrients and healthy for organic plants 126.

In order for earthworms 124 to thrive in soils 122, a proper humidity must be maintained. Sensor 161 detects the temperature and humidity from a middle carousel 120. However, it is rather difficult to control temperatures of BIoTower™ 100 outdoor. In an exemplary embodiment of the present invention, both the temperature and humidity data from sensor 161 are received and observed over a cloud-based storage (not shown). However, only humidity is controlled. Processor 160 receives the humidity data from sensor 161 and compares them with a preset value ($H_p$). If the measured humidity ($H_m$) are lower than the preset value, a cloud based computing facility informs processor 160 to turn on motor 15588 of water pump 154 to pump water from water container 140 to ring sprinkler 152. Water is released from ring sprinkler through plurality of holes 153. Water permeates from top carousel to the bottom carousel 120, providing a thriving condition with the right amount of moisture for earthworms 124, organic plants 126, and soil 122. The measured humidity (Hm) provides the proper amount of moisture for earthworms 124.

Continuing with the operation of BIoTower™ 100 as shown in FIG. 1 and FIG. 7, in one exemplary embodiment, water container 140 further includes a fine mesh lid 145 to collect worm castings and prevent insects. Water filter 156 is designed to filter out materials which may expel earthworms 124 such as oils, woods, and other hard materials, etc.

Figure 8:
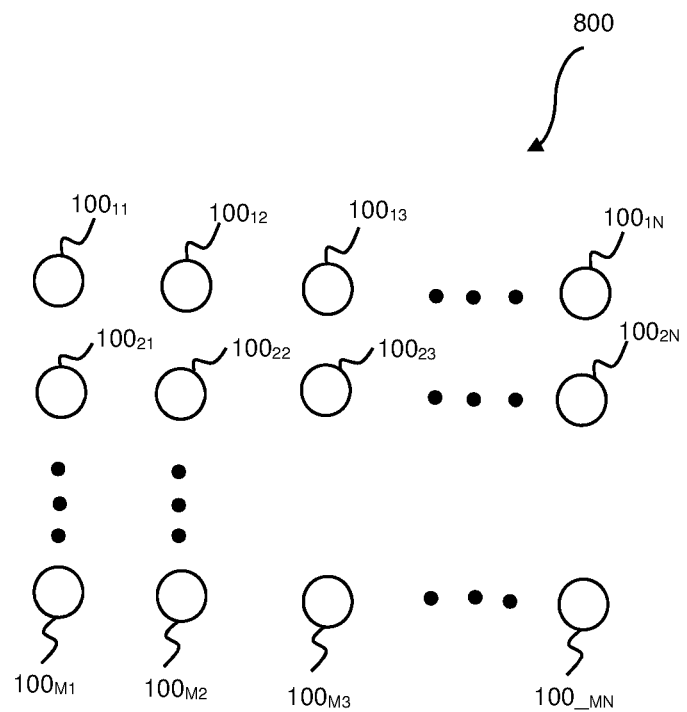
FIG. 8 is an array of BIoTower™ in accordance with an exemplary embodiment of the present invention.

According to various aspects, referring to FIG. 8, a diagram of an array 800 of M×N BIoTowers™ 100 described in FIG. 1-FIG. 7 is illustrated. In an exemplary embodiment of the present invention, BIoTower™ 100 are arranged into an array that includes N×N BIoTowers™ 100. In the first row, the first BIoTower™ in the array 800 is $100_{11}$, the second BIoTower™ is $100_{1N}$. In the second row, the first BIoTower™ is $100_{21}$, the second BIoTower™ is $100_{21}$, and the $N^{th}$ BIoTower™ is $100_{2N}$. In the $M^{th}$ row, the first BIoTower™ is $100_{M1}$, and the $N^{th}$ BIoTower™ is $100_{MN}$.

Continuing with FIG. 8, each processor 160, and sensor 161, water pump 154, motor 155 has a unique identification so that the cloud based computing and storage services can distinguish humidity and temperature data from each BIoTower™ 100$ij$, where i represents the row, I=1, 2, . . . , M; and j represents the column 1, 2 . . . , N of array 800.

Figure 9:
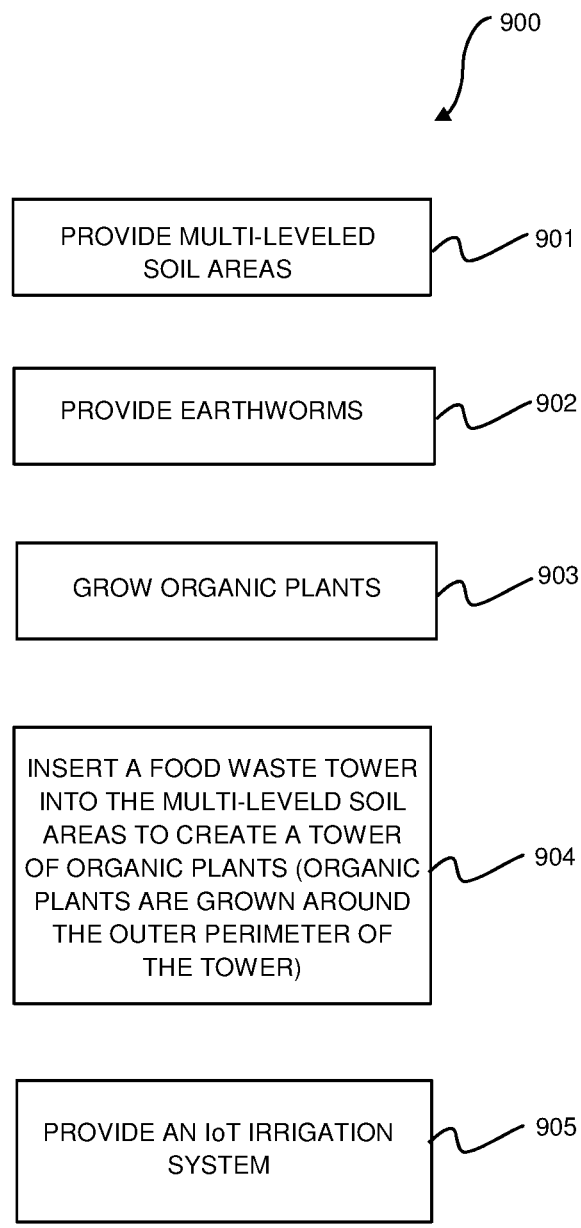
FIG. 9 is a flow chart illustrating a method for recycling food wastes into nutrients and for growing organic plants in accordance with an exemplary embodiment of the present invention.

Finally referring to FIG. 9, a method 900 for separating and recycling foods wastes into bio-fertilizers for growing organic plants is illustrated.

At step 901, soil areas are provided to grow organic plants. Step 802 is realized by multi-leveled carousel 120 as shown and discussed in FIG. 1 and FIG. 7.

At step 902, earthworms are provided to the soil areas.

At step 903, organic plants are grown on the earthworms infested soil areas. Step 908 is realized by organic plants 126 and BIoTower™ 100.

At step 904, food waste areas with entry and exit openings are inserted into the soil areas so that earthworms can enter to digest the food wastes and return to excrete nutrient-rich fertilizer for organic plants. Step 904 is realized by food waste disposable tower 110 as illustrated in FIG. 1 and FIG. 7.

Finally, at step 905, food waste areas is equipped with an Internet of Things (IoT) irrigation system. Step 905 is realized by IoT irrigation system including water container 140, water tube 151, ring sprinkler 152, water pump 154, motor 185, water filter 156, humidity and temperature sensor 161, motor 155 that operates water pump 154, IoT processor 160 that communicates with sensor 161 and controls water pump 154 using IoT and cloud based serves. Temperature and humidity data are collected to the IoT processor, and humidity is constantly maintained to provide a thriving condition for earthworms.

The foregoing description has been directed to specific embodiments. It will be apparent, however, that other variations and modifications may be made to the described embodiments, with the attainment of some or all of their advantages. For instance, it is expressly contemplated that the control of each element of array 800 using IoT technology and method 900 described herein can be implemented as software being stored on a tangible (non-transitory) computer-readable medium (e.g., disks/CDs/RAM/EEPROM/ etc.) having program instructions executing on a computer, hardware, firmware, or a combination thereof. Accordingly this description is to be taken only by way of example and not to otherwise limit the scope of the embodiments herein. Therefore, it is the object of the appended claims to cover all such variations and modifications as come within the true spirit and scope of the embodiments herein.

The foregoing description details certain embodiments of the invention. It will be appreciated, however, that no matter how detailed the foregoing appears in the text, the invention can be practiced in many ways. As is also stated above, it should be noted that the use of particular terminology when describing certain features or aspects of the invention should not be taken to imply that the terminology is being redefined herein to be restricted to including any specific characteristics of the features or aspects of the invention with which that terminology is associated. The scope of the invention should, therefore, be construed in accordance with the appended claims and any equivalents thereof.

DESCRIPTION OF NUMERALS

110 food waste disposable tower
116 entry and exit openings for earth worms
112 top cap for food waste disposable tower
114 bottom cap for food waste disposable tower
120 multi-leveled carousels
122 soils where organic plants are grown
124 earth worms
126 organic plants
130 food wastes
140 water tank
141 ball float valve
142 ball float
145 fine mesh retainer
151 water tube
152 sprinkler ring
153 water releasing hole
154 water pump
155 motor for water pump
156 water filter
160 processor
161 temperature and humidity sensors
209 controller box
210 supporting pole
211 electrical cord
220 base
310 hollow core of each carousel
311 exhaustion holes for top cap of food waste disposable tower
320 section of each carousel
321 section divider
401 top surface of base
402 rail
403 insertion hole where food waste disposable tower is inserted
405 supporting legs
510 solar panel
511 solar cell
521 battery
800 array of BIoTower™

What is claimed is:

1. A bio-tower for growing organic plants, comprising:
a food waste disposal tower for receiving food wastes;
multi-leveled carousels, connected to and radiating outward from an outer circumference of said food waste disposal tower, each carousel adapted to contain earthworms-infested soils for growing said organic plants; and
an Internet-of-Thing (IoT) based irrigation system adapted to provide water to said earthworms-infested soils so as to maintain a proper humidity for said organic plants and earthworms, wherein said food waste disposal tower includes a plurality of exit and entry openings designed for said earthworms to enter to digest said food wastes and return to said multi-leveled carousels to excrete nutrients that fertilize said organic plants, wherein said Internet-of-Thing (IoT) based irrigation system further comprises a controller configured to provide water to said earthworms-infested soils upon wirelessly receiving temperature and humidity data from sensors coupled to said multi-leveled carousels using an Internet of Things (IoT) technology.

2. The bio-tower of claim 1 wherein said food waste disposal tower has a hollow cylindrical shape that includes a top side, a bottom side, and a lateral side, and wherein said top side is adapted to receive said food wastes, said bottom side includes drainage openings to drain out liquid food wastes, and wherein said plurality of exit and entry openings are formed on the outer perimeter of said lateral side.

3. The bio-tower of claim 1 wherein said multi-leveled carousels further comprises a top carousel, at least one middle carousel, and a bottom carousel vertically stacked on top of one another around the outer perimeter of said food waste disposal tower.

4. The bio-tower of claim 1 wherein each of said multi-leveled carousels comprises a circular opening at the center through which said food waste disposable tower is inserted, wherein each of said multi-leveled carousels includes a plurality of petal-shaped containers extending outward from said circular opening, wherein each of said plurality of petal shaped containers is adapted to contain said earthworms-infested soils and said earthworms.

5. The bio-tower of claim 4 further comprising a foot stand, placed directly underneath said bottom carousel, configured to support said multi-leveled carousels.

6. The bio-tower of claim 5 further comprising: a water tank, and wherein said foot stand is a three-legged stool having a second opening at the center through which said food waste disposal tower is inserted, wherein said second opening is concentric and has the same area as said circular opening.

7. The bio-tower of claim 6 wherein water tank comprises:
a water inlet; and
a ball float valve, connected to said water inlet, designed to refill said water tank.

8. The bio-tower of claim 1 wherein said IoT based irrigation system further comprises:
- a water pipe having a first end;
- a ring water sprinkler connected to a second end opposite to said first end of said water pipe;
- a water pump, connected to said first end of said water pipe, operable to pump water from said water tank to said ring water sprinkler;
- a motor connected to said water pump;
- a water filter, placed in said water tank and connected to said water pump, and
- said sensors comprising a temperature and humidity sensor placed in said at least one middle carousels operable to sense said humidity and temperature data from said at multi-leveled carousels.

9. The bio-tower of claim 8 wherein said water ring sprinkler includes a plurality of holes punctured around the perimeter of said water ring sprinkler for releasing water to said top carousel.

10. The bio-tower of claim 9 wherein said IoT based irrigation system further comprises:
- a solar panel; and
- a battery connected to said solar panel operable to provide power supply to said controller.

11. The bio-tower of claim 10 further comprising a remote device electrically in communication with said controller for receiving said temperature and humidity data from said multi-leveled carousels.

12. The bio-tower of claim 11 wherein said controller and said IoT based irrigation system are configured to communicate to each other using said Internet of Things (IoT) technology via a cloud network.

13. The bio-tower of claim 11 wherein said remote device is a cellular telephone.

14. A method for encouraging the separation of organic wastes and growing of organic plants using a bio-tower, comprising;
- (e) providing worm-infested soil areas in said bio-tower where said organic plants are grown;
- (f) providing a food waste area;
- (g) aesthetically arranging earthworm-infested soils around said food waste area so that the growing of said organic plants encourage the discarding of said food wastes into said food waste area, wherein said food waste area having a plurality of exit and entry openings so that earthworms are able to enter said food waste area to digest said food wastes and return to said earthworm-infested soils to deposit nutrients into said earthworm-infested soils; and
- (h) remotely providing humidity to said worm-infested earthworm infested soils, said organic plants, and said earthworms using an Internet of things (IoT) based irrigation system;

wherein said bio-tower further comprises a food waste disposal tower for receiving said food wastes; and multi-leveled carousels connected to said food waste disposal tower, each carousel adapted to contain earthworms-infested soils for growing said organic plants, wherein said Internet-of-Thing (IoT) based irrigation system further comprises a controller configured to provide water to said earthworms-infested soils upon wirelessly receiving temperature and humidity data from sensors coupled to said multi-leveled carousels using an Internet of Things (IoT) technology.

15. The method of claim 14 wherein said Internet-of-Thing (IoT) based irrigation system is adapted to provide water to said worm-infested soils so as to maintain a proper humidity for said organic plants and said earthworms, wherein said food waste disposal tower includes a plurality of exit and entry openings designed for said earthworms to enter to digest said food wastes and return to said multi-leveled carousels to excrete nutrients that fertilize said organic plants.

16. The method of claim 14 wherein said step of providing a food waste area further comprises:
- providing a hollow cylindrical container into which said multi-leveled carousels are inserted, each of said carousels has containers that extend outward from the outer perimeter of said cylindrical container; and
- providing said plurality of exit and entry openings around the perimeter of said hollow cylindrical container.

17. The method of claim 14 wherein said step of remotely providing humidity to said worm-infested soil area further comprises:
- measuring the temperature and humidity of said earthworm-infested soils;
- sending said temperature and humidity of said earthworm-infested soils to a remote device; and
- if said humidity is less than a preset humidity, providing water to said earthworm-infested soils using commands from said remote device to said controller.

18. The method of claim 17 wherein said step of remotely providing humidity to said earthworm-infested soils further comprising:
- providing a solar panel adapted to charge a battery;
- providing a water pump; and
- providing a remote controlled valve.

19. The method of claim 17 wherein said steps of controlling the temperature and humidity of said earthworm-infested soils via a remote device further comprises:
- providing a water tank for said multi-leveled carousels;
- checking the water level of said water tank; and
- refilling said water tank with water from an external source using a ball float valve.

20. The method of claim 17 wherein said IoT based irrigation system and said controller are configured to communicate to each other using said Internet of Things (IoT) technology via a cloud network.

\* \* \* \* \*